United States Patent
Peters et al.

(10) Patent No.: US 7,713,224 B1
(45) Date of Patent: May 11, 2010

(54) ANKLE BRACE

(75) Inventors: Rick Peters, Indianapolis, IN (US); Randolph Smith, Indianapolis, IN (US)

(73) Assignee: Ultra Athlete LLC, Indianapolis, IN (US)

( * ) Notice: Subject to any disclaimer, the term of this patent is extended or adjusted under 35 U.S.C. 154(b) by 896 days.

(21) Appl. No.: 11/535,829

(22) Filed: Sep. 27, 2006

(51) Int. Cl.
*A61F 5/00* (2006.01)
(52) U.S. Cl. .............. 602/23; 602/27; 128/882
(58) Field of Classification Search .......... 602/23, 602/26–27, 4; 128/882
See application file for complete search history.

(56) References Cited

U.S. PATENT DOCUMENTS

| | | | |
|---|---|---|---|
| 4,517,968 A | 5/1985 | Greene et al. | |
| 4,834,078 A | 5/1989 | Biedermann | |
| 4,865,023 A | 9/1989 | Craythorne et al. | |
| RE33,395 E | 10/1990 | Peters | |
| 4,962,760 A * | 10/1990 | Jones | 602/27 |
| 5,069,202 A | 12/1991 | Prock | |
| 5,445,603 A | 8/1995 | Wilkerson | |
| 5,496,263 A * | 3/1996 | Fuller et al. | 602/27 |
| 5,797,865 A | 8/1998 | McDavid, III | |
| 5,944,678 A | 8/1999 | Hubbard | |
| 6,056,712 A * | 5/2000 | Grim | 602/27 |
| 6,186,966 B1 | 2/2001 | Grim et al. | |
| 6,602,215 B1 | 8/2003 | Richie, Jr. | |
| 6,689,081 B2 | 2/2004 | Bowman | |
| 6,767,332 B1 | 7/2004 | Pardue et al. | |
| 6,929,617 B2 | 8/2005 | McCormick et al. | |
| 2003/0153852 A1* | 8/2003 | Hinshon | 602/6 |
| 2004/0019307 A1* | 1/2004 | Grim et al. | 602/27 |

* cited by examiner

*Primary Examiner*—Michael A. Brown
(74) *Attorney, Agent, or Firm*—Cameron and Associates; Theresa Fritz Camoriano

(57) ABSTRACT

An ankle brace is made to be very comfortable and easy to use while still providing sufficient support.

15 Claims, 11 Drawing Sheets

ANKLE BRACE

BACKGROUND

The present invention relates to ankle braces.

DETAILED DESCRIPTION

Figure 1:
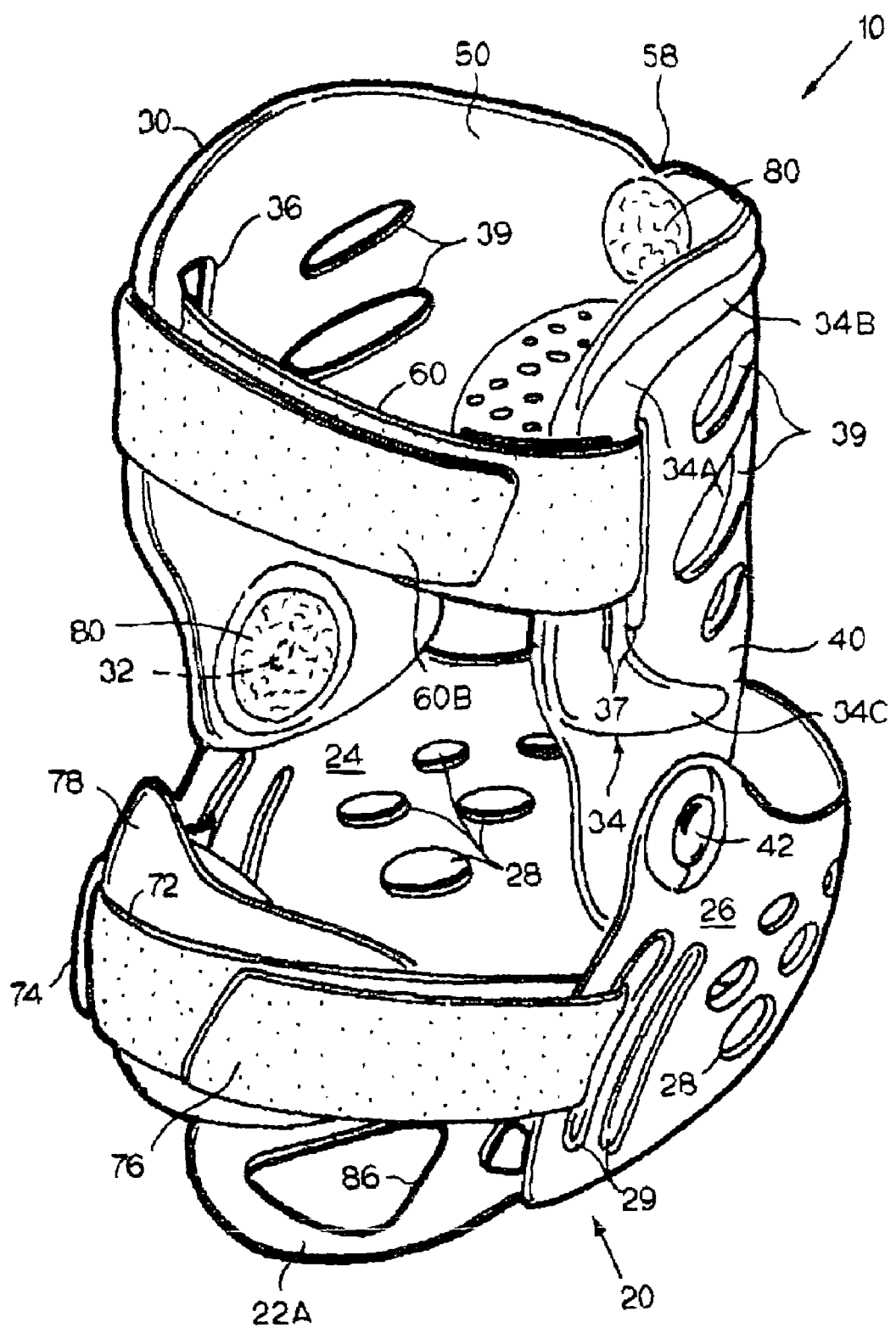
FIG. 1 is a front perspective view of one embodiment of an ankle brace made in accordance with the present invention.

FIGS. 1-8 show one embodiment of an ankle brace 10 made in accordance with the present invention. The basic components of the ankle brace are a substantially U-shaped stirrup 20, a left pivot leg 30, and a right pivot leg 40. The stirrup 20 includes a bottom portion 22, a left upright portion 24, and a right upright portion 26. When worn, the bottom portion 22 extends under the wearer's foot, and the left and right upright portions 24, 26 extend upwardly along the left and right sides of the wearer's foot, respectively. A forward projection 22A on the bottom portion 22 is substantially thinner and more flexible than the rest of the stirrup 20, providing for the wearer's comfort. The left and right pivot legs 30, 40 are pivotally attached to the left and right upright portions 24, 26 at left and right pivot points 32, 42, respectively, and are connected together by a rear cuff 50, which extends around the rear of the wearer's leg. The left and right sides of the brace 10 are mirror images of each other, except that the right pivot leg 40 has two vertical slots 37 for receiving an upper adjustment strap 60, while the left pivot leg 30 has only one vertical slot 36 for receiving the upper adjustment strap 60.

This particular ankle brace 10 is made of a polyester-based thermoplastic polyurethane (TPU) resin made by Bayer MaterialScience LLC and sold under the name Texin® 255. This material has a flexural modulus of 20,000 psi at 73 degrees Fahrenheit (a.k.a. room temperature) and a tensile strength of 7,000 psi. A known standard test that is used to determine the flexural modulus of a given material is ASTM D 790, and a standard test for determining the tensile strength is ASTM D412. The flexural modulus for the materials such as polypropylene and nylon that are typically used for prior art rigid braces is well over 100,000 psi. For example, a flexural modulus for polypropylene is typically over 110,000 psi, and may be as high as 600,000 psi. A flexural modulus for nylon is typically over 130,000 psi, and may be as high as 1,200,000 psi. Because the brace 10 is more flexible than prior art rigid braces, it is able to conform more closely to the shape of the wearer's foot. This means that, in many cases, in addition to being more comfortable, it actually can provide better support than a more rigid brace. Prior art wraps, such as "Ace" bandages, also are able to conform to the shape of the wearer's foot, but they are too flexible to provide good support. For comfort and support, it is preferable to use a material having a flexural modulus at room temperature (73° F.) between 10,000 psi and 80,000 psi, and more preferable between 10,000 psi and 50,000 psi. It is also desirable for the material to have a tensile strength greater than 4,000 psi in order to maintain structural integrity.

It would be possible to make portions of the brace 10 from different materials, if desired. For example, it would be possible to make the right and left pivot legs 30, 40 from polyurethane and to make the stirrup portion 20 of the brace from traditional, more rigid materials, or the reverse. Of course, other materials besides polyurethane could be used to provide the desired flexural modulus and tensile strength.

Figure 2:
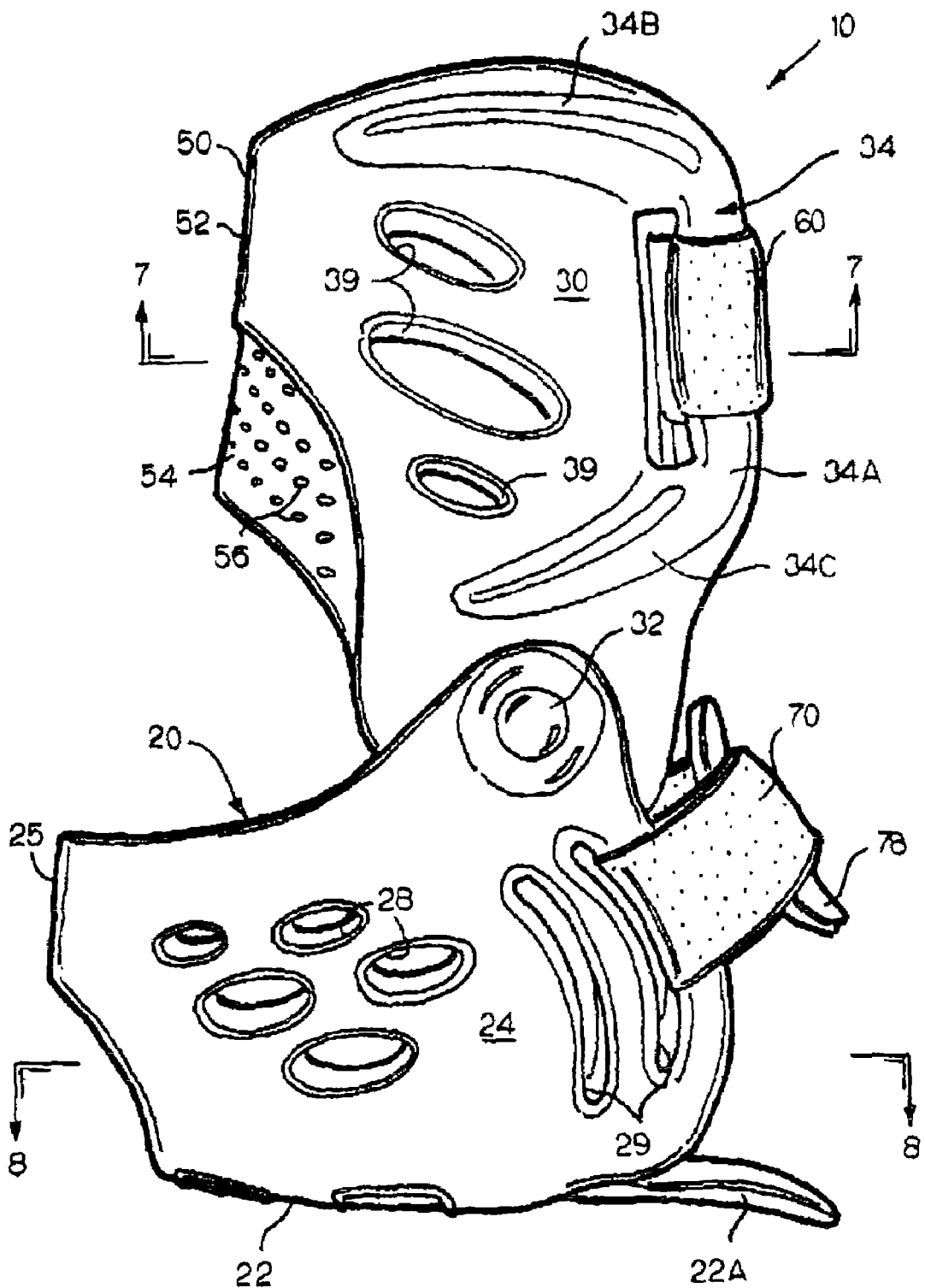
FIG. 2 is a left side view of the ankle brace of FIG. 1.
Figure 7:
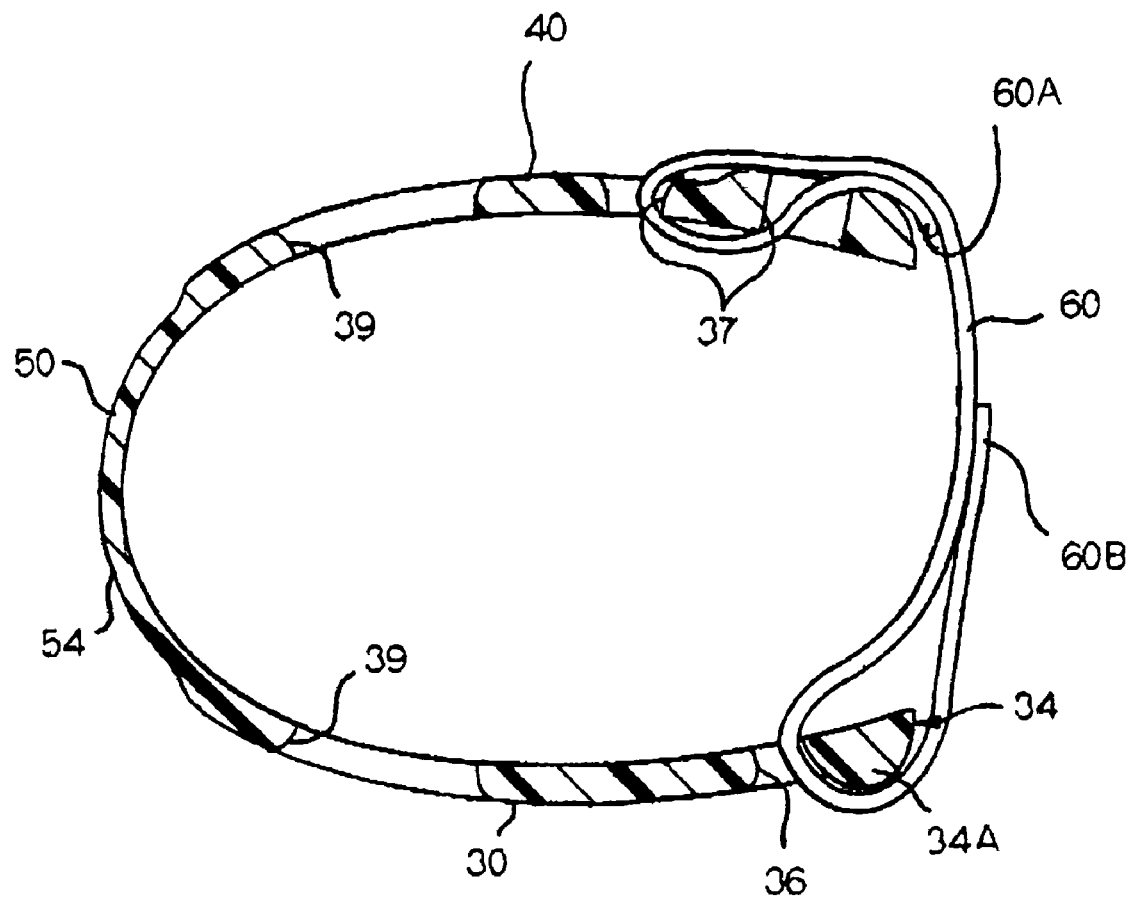
FIG. 7 is a view taken along line 7-7 of FIG. 2.

As best shown in FIGS. 2 and 7, the major portion of the left pivot leg 30 is relatively thin, and there is a raised, U-shaped rib 34 near the front of the leg 30. The right pivot leg 40 is almost a mirror image of the left pivot leg 30, with the only difference being that it has two vertical slots 37, with the front slot being cut through the rib 34A. The U-shaped rib 34 includes a first portion 34A, that extends generally in a top to bottom direction along the front of the pivot leg 30, and second and third portions 34B, 34C that extend generally rearwardly from the top and bottom of the first portion 34A. The major portion of the pivot leg 30 preferably is between 0.050 and 0.150 inches thick, and the U-shaped rib 34 is tapered, being thinner where it blends into the rest of the leg 30 and thicker in the middle. The thickest portion of the rib 34 preferably is between 0.150 inches and 0.250 inches thick. FIG. 7 best shows that the first portion 34A of the rib 34 is thicker than the major portion of the pivot leg 30.

Referring again to FIGS. 2 and 7, the left pivot leg 30 defines a vertical slot 36 rearwardly and general parallel to the first portion 34A of the rib 34. The slot 36 extends between the second portion 34B and third portion 34C of the rib. The slot 36 receives the upper adjustment strap 60, which includes hook and loop fastener material, such as Velcro®, which is used to tighten the pivot legs 30, 40 against a wearer's leg when in use. As best shown in FIG. 7, the right end 60A of the strap 60 is fed through the two slots 37 in the right pivot leg 40, with the first end of the strap 60 lying forward of the front or first vertical slot 37, and the strap 60 then extends into the first or front vertical slot 37 and out the second or rear vertical slot 37 and wraps over the first end of the strap, and then the central portion of the strap 60 extends across the front of the brace between the two pivot legs 40, 30, with the central portion of the strap 60 extending across the front opening between the two pivot legs 40, 30, and the second end of the strap 60 extends through the vertical slot 36, and then wraps back around the front of the brace onto the central portion of the strap 60, where it is secured to the front side of the central portion of the strap by means of the hook and loop fastener. Friction prevents the right end 60A of the strap from coming loose from the right pivot leg 40, and the hook and loop fastener secures the other end 60B of the strap 60 in place. The main function of the rib 34 is to beef up the slot portion of the brace in order to withstand the forces from the strap 60.

Figure 4:
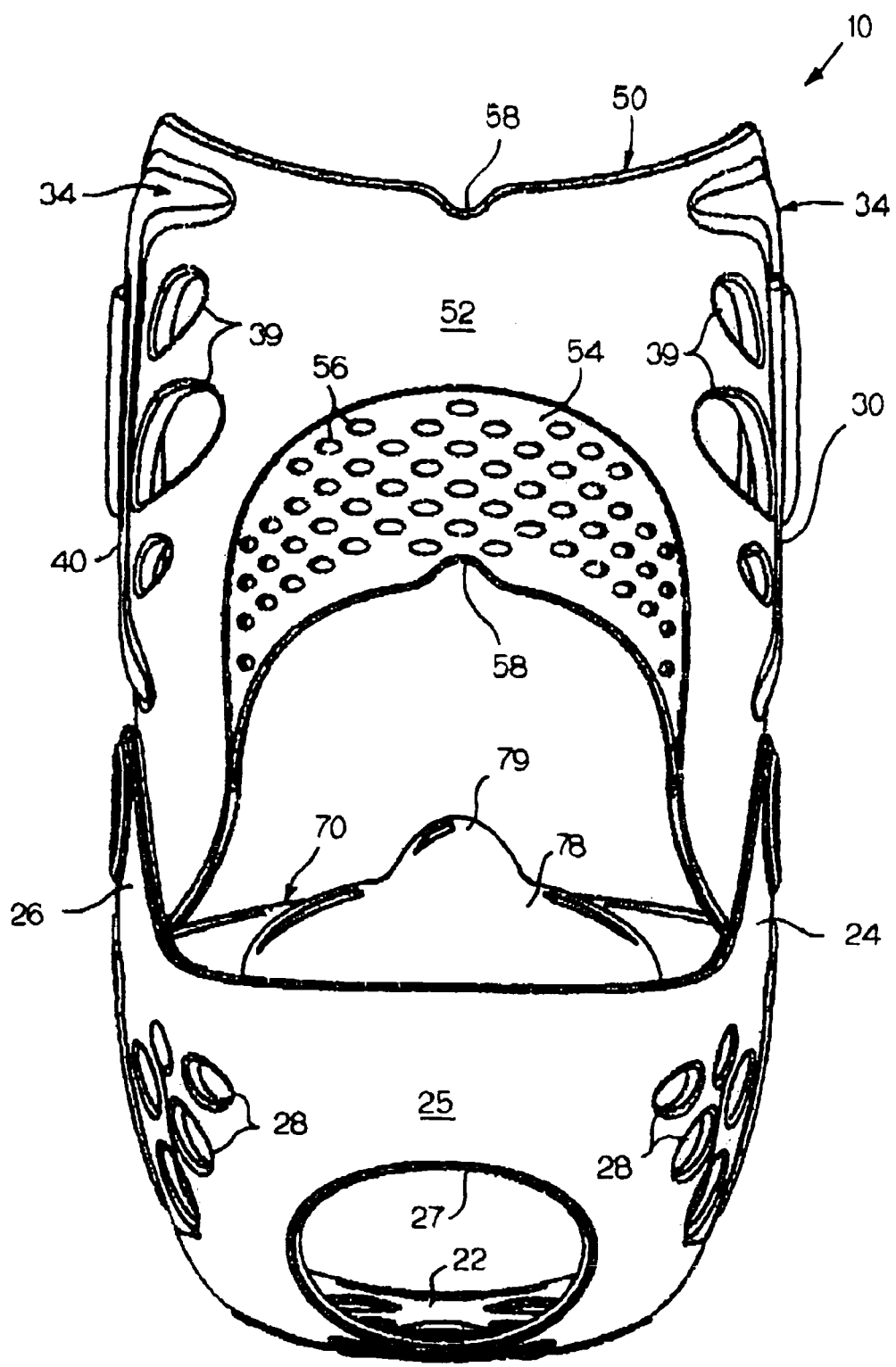
FIG. 4 is a rear view of the ankle brace of FIG. 1.

The right and left pivot legs 30, 40 are connected together in a unitary piece by a cuff 50, which extends around the rear side of the ankle brace 10. (Alternatively, it would be possible to provide a cuff that extends around the front side of the brace or to eliminate the cuff completely.) As best shown in FIG. 4, the cuff 50 includes upper and lower bands 52, 54 having different thicknesses. The lower band 54 is thinner than the upper band 52, with the upper band having a thickness in the same range as the right and left pivot legs 30, 40, and the lower band 54 preferably being between 0.030 inches and 0.050 inches thick. This allows the lower portion of the cuff 50 to be more flexible and the upper portion to provide more support, which helps make the brace 10 more comfortable for the wearer. Of course, the entire cuff 50 could be made of a single thickness, or the thickness of the cuff could vary throughout the cuff, if desired.

The lower band 54 also defines a plurality of openings 56, which are slightly elongated in the left to right direction. The cuff 50 also has vertical indentations 58 at the center top and bottom edges, which reduce the height of the cuff at its center, making it easier for the cuff 50 to flex about a vertical axis at its center.

As best shown in FIG. 2, the right pivot leg 30 defines larger elongated openings 39, which extend in a generally front to back direction, with the front of each opening 39 being a bit lower than the rear. The number, size, and arrangement of the openings 39 may be selected by the designer as desired.

As best shown in FIG. 2, the right upright portion 24 of the stirrup 20 also includes elongated openings 28 which are generally elongated in the front to back direction.

Figure 3:
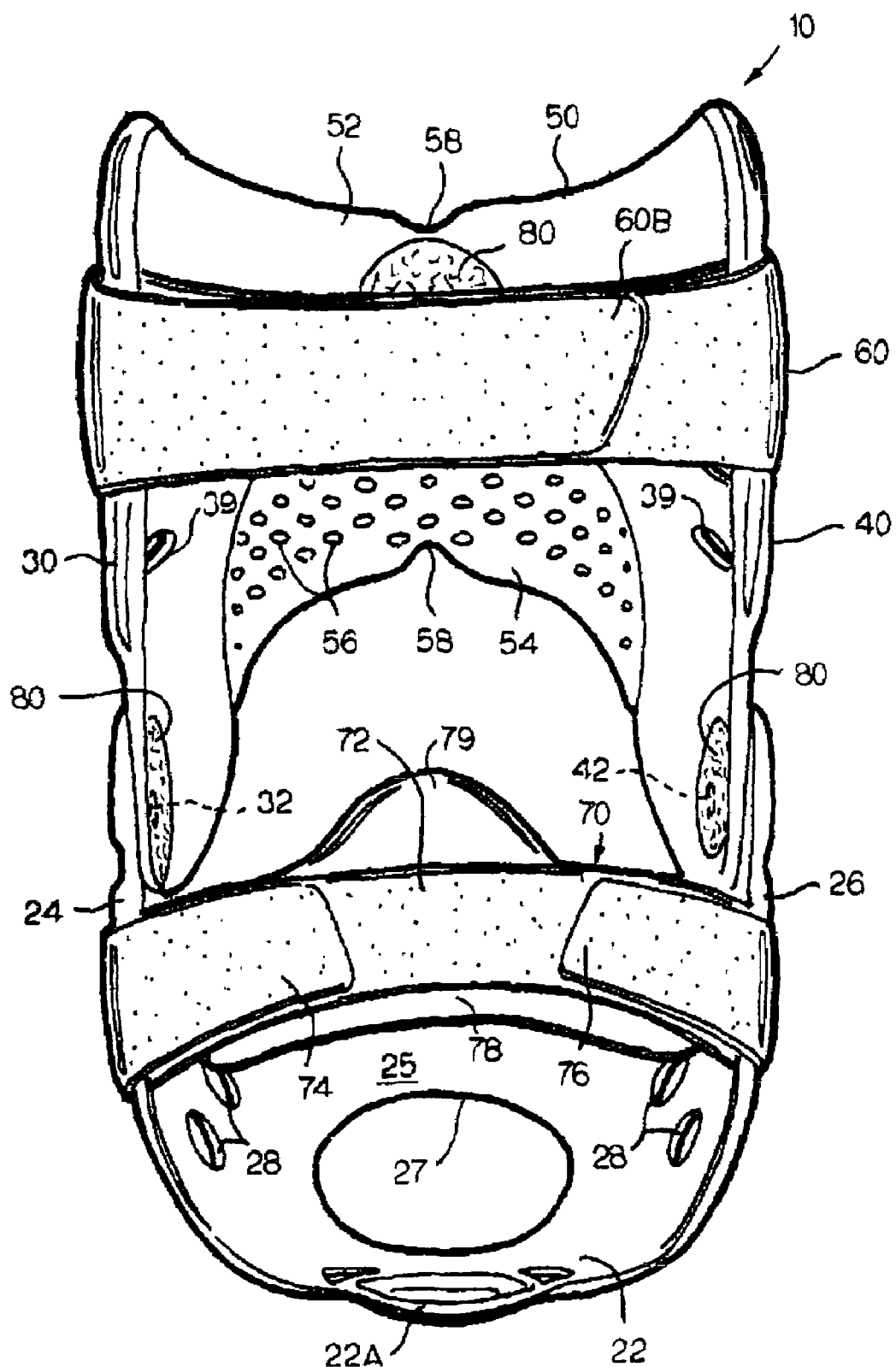
FIG. 3 is a front view of the ankle brace of FIG. 1.
Figure 5:
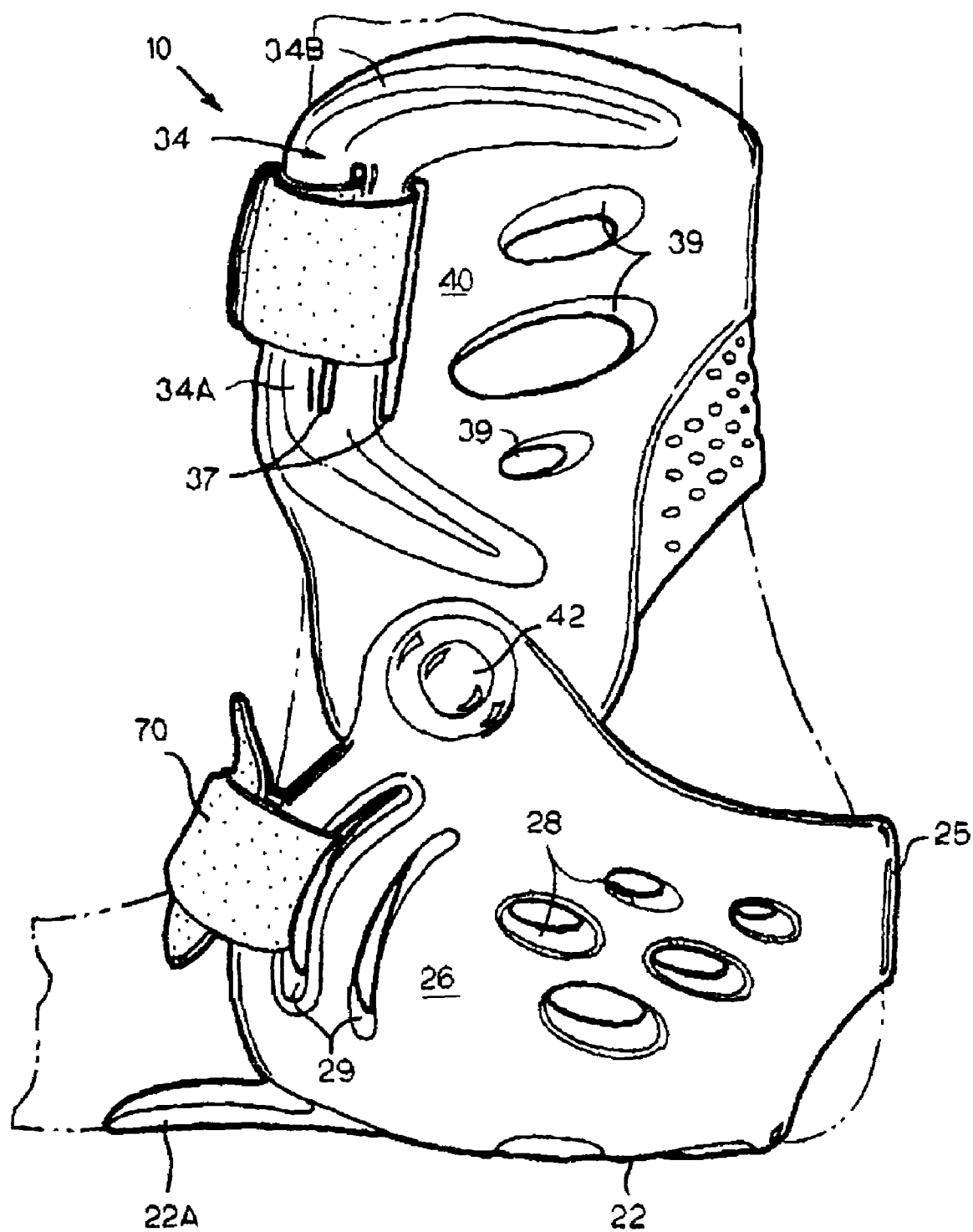
FIG. 5 is a right side view of the brace of FIG. 1 being worn on a human foot.

As best shown in FIGS. 3 and 4, the left and right upright portions 24, 26 are connected at the rear by a heel strip 25. The heel strip 25 and left and right upright portions 24, 26 define a rounded heel opening 27, which receives the wearer's heel, as shown in FIG. 5.

The left and right upright portions 26, 24 also define arcuate slots 29 near their front edge. In this case, two parallel slots 29 are defined by the left upright portion 26, and two parallel slots are formed by the right upright portion 24. The slots 29 receive a lower adjustment strap 70, which is used to tighten the left and right upright portions 24, 26 of the stirrup 20 to the wearer's foot.

Figure 6:
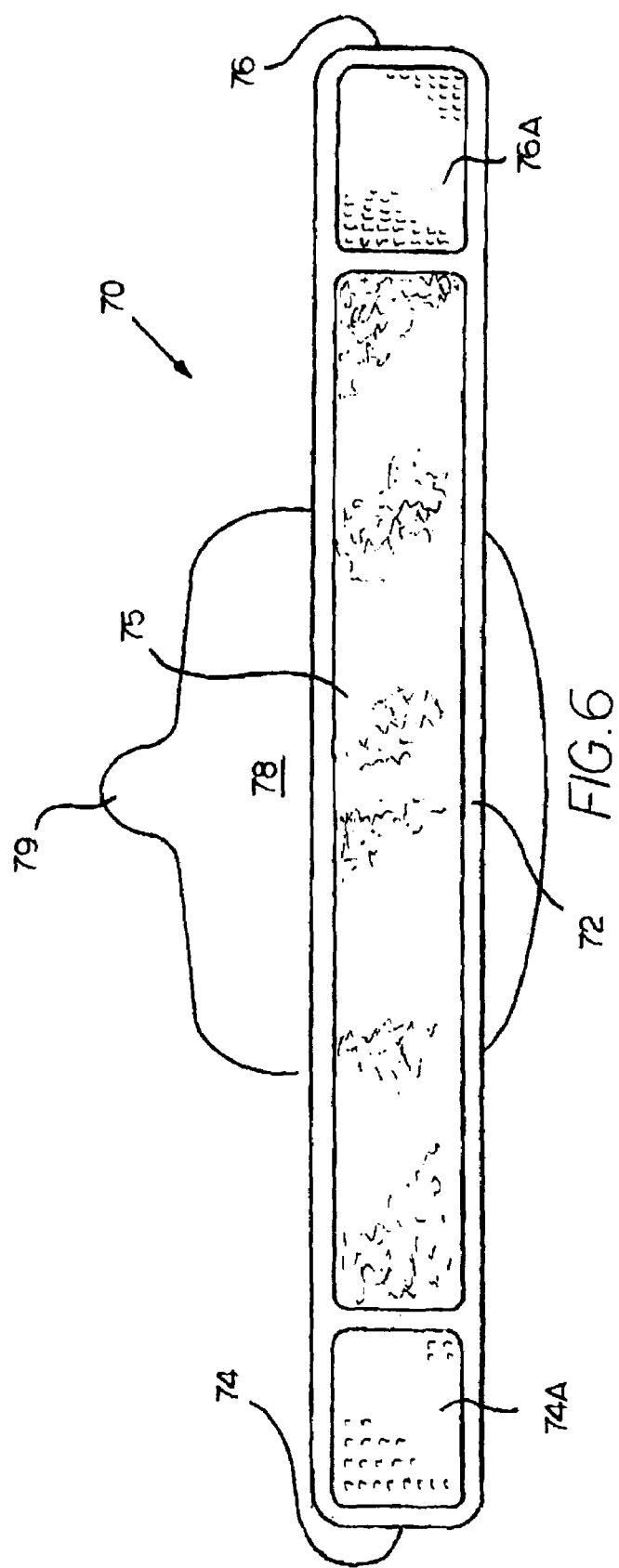
FIG. 6 is a front view of the lower adjustment strap of FIG. 1 in the open position, removed from the ankle brace.

The lower adjustment strap 70 is shown in more detail in FIG. 6 and includes a middle portion 72, a left end 74, and a right end 76. On the top surface of the lower adjustment strap 70 is hook and loop fastener material. In this embodiment, there are hook portions 74A, 76A near each end 74, 76, and a loop portion 75 extending between the hook portions 74A, 76A through the middle portion 72. There is also a cushion 78 secured to the rear surface of the middle portion 72 of the adjustment strap 70, and the middle portion of the cushion 78 defines an upwardly-extending tongue 79.

In use, the adjustment strap 70 functions in a very similar manner to a lace-up shoe. The left end 74 of the adjustment strap 70 is inserted through a slot 29 in the left upright portion 24 of the stirrup 20, and the right end 76 of the adjustment strap 70 is inserted through a slot 29 in the right upright portion 26 of the stirrup 20. The wearer puts on the ankle brace, pulls up on the tongue 79 and pulls both ends 74, 76 of the strap 70 toward the middle, where each of the hook portions 74A, 76A engages with the loop portion 75. This differs from a typical strap arrangement, in which one side of the strap is fixed to the brace, and there is only one free end of the strap, which is pulled in order to tighten the strap. Since this arrangement allows the wearer to pull on both ends of the strap 70 simultaneously in order to tighten the strap 70, the forces are applied more evenly and more like tightening the laces on a shoe. In fact, this arrangement could be used on other types of footwear that include a U-shaped stirrup, such as a shoe, in the same manner that it is used on this brace 10. The reason for the second set of slots 29 is to provide for additional adjustment, allowing the wearer to decide which set of slots is to be used.

Figure 6A:
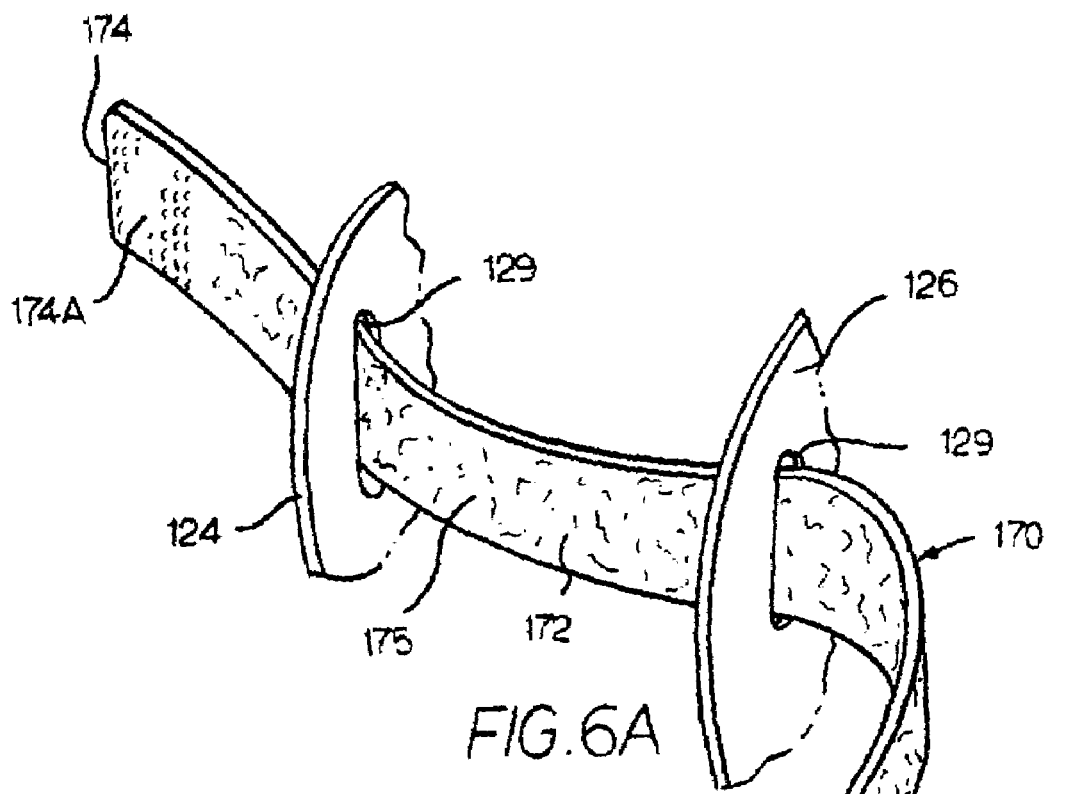
FIG. 6A is a view of another strap that may be used to tighten the ankle brace of FIG. 1.
Figure 6B:
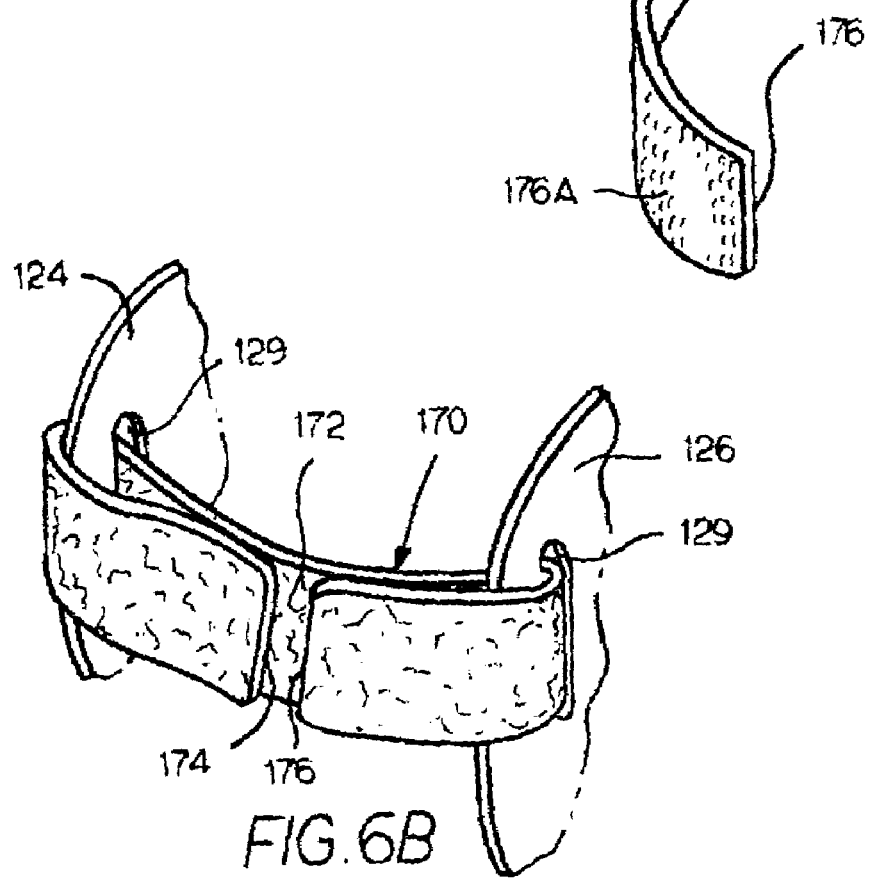
FIG. 6B is a view of the strap of FIG. 6A, showing one manner of tightening the strap.
Figure 6C:
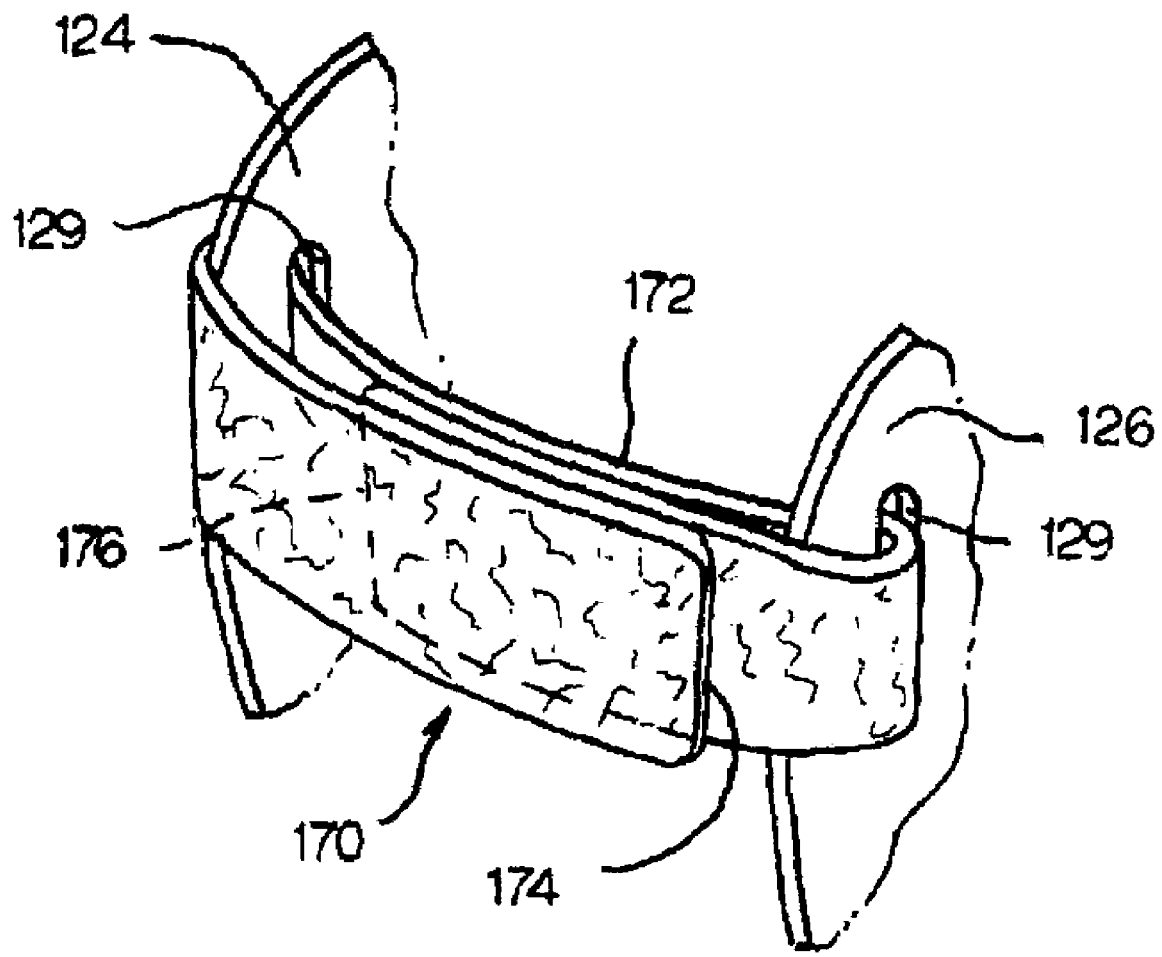
FIG. 6C is a view of the strap of FIG. 6A, showing a second manner of tightening the strap.

FIGS. 6A-6C show an alternate embodiment of an adjustment strap 170 that may be used with the ankle brace 10 (or with other articles of footwear). The article of footwear includes left and right upright side portions 124, 126, each defining at least one slot 129, as shown in FIGS. 6A-6C. Like the previous embodiment, the adjustment strap 170 includes a middle portion 172, a left end 174 and a right end 176, and on the top surface of the strap 170 there are hook portions 174A, 176A near each end 174, 176, and a first loop portion 175 extending through the middle portion 172 between the hook portions 174A, 176A. However, unlike the previous embodiment, there is no separate cushion in the central portion of the adjustment strap 170 and no tongue 79. In this embodiment, the entire back surface of the strap is covered by a second loop portion 177, which acts as a cushion and provides an additional surface to which one of the ends of the strap may be fastened, as will be explained in more detail later.

FIG. 6A is a view of the strap in its open position. The left end 174 of the strap 170 has been inserted through the slot 129 in the left portion 124, and the right end 176 of the strap 170 has been inserted through the slot 129 in the right portion 126. To tighten the brace around his foot, the wearer pulls the left and right ends 174, 176 of the strap simultaneously until there is a snug fit. Then, the wearer folds the left and right ends 174, 176 back over the middle portion 172 and fastens the left and right portions onto the strap 170 by means of the hook and loop fastener.

In FIG. 6B, the left and right ends 174, 176 are secured to the middle portion 172 by engaging each of the hook portions 174A, 176A (not visible in FIG. 6B) with the first loop portion 175 on the top surface of the strap 170. In FIG. 6C, the left and right ends 174, 176 overlap, with the right end 176 being secured to the middle portion 172 and the left end 174 being secured on top of the right end 176. Of course, the user could arrange the same strap 170 in reverse, with the left end being secured to the middle and then the right end being secured on top of the left end. In the arrangement shown in FIG. 6C, the hook portion 176A (not visible in FIG. 6C) near the right end 176 is engaged with the loop portion 175 on the top surface of the middle portion 172 of the strap 170, and the hook portion 174A (also not visible in FIG. 6C) near the left end 174 is engaged with the second loop portion 177 on the back of the right end 176 of the strap 170.

Figure 8:
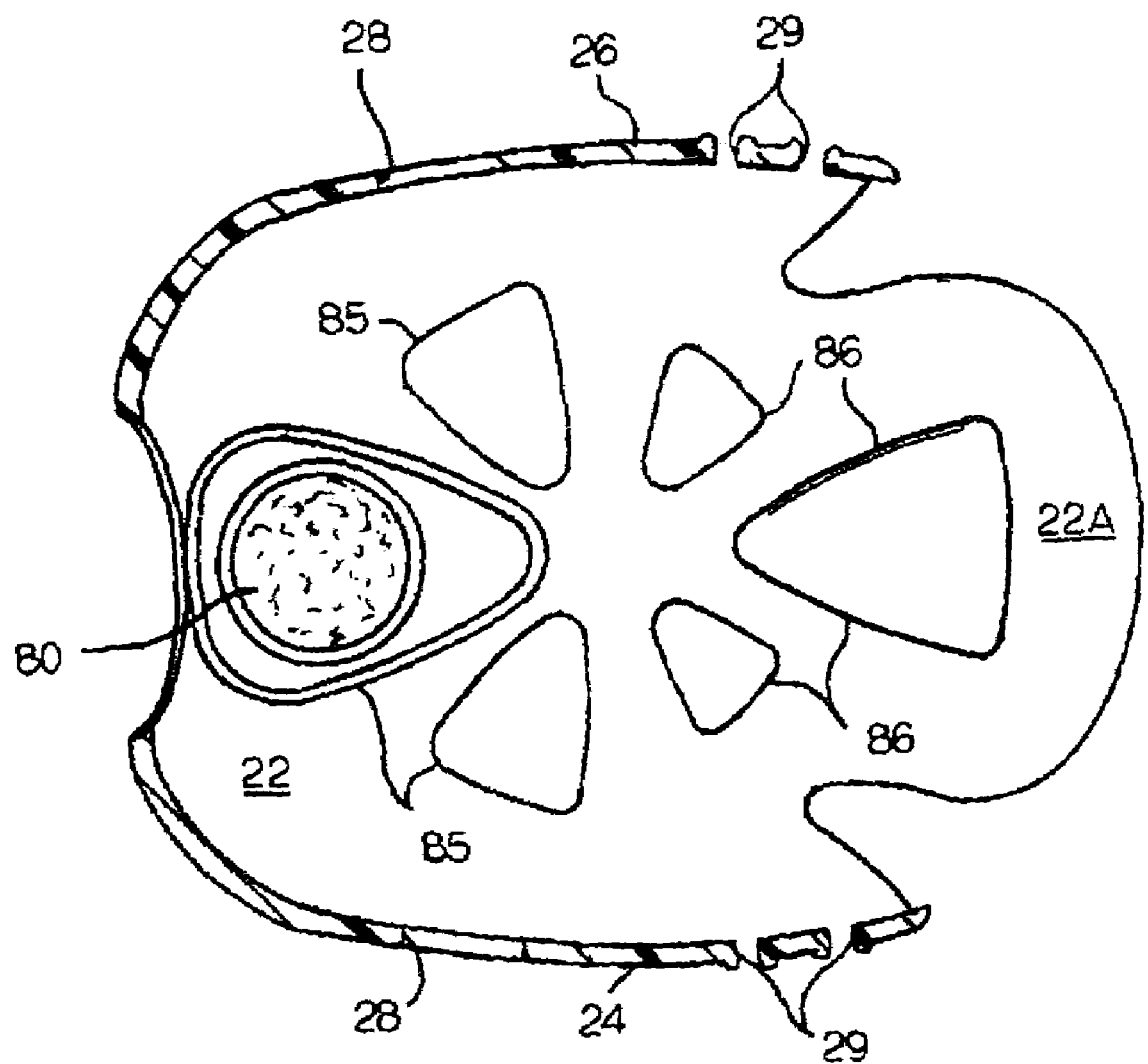
FIG. 8 is a view taken along line 8-8 of FIG. 2.

It should be noted that various forms of additional cushioning could be added between the ankle brace 10 and the wearer's ankle, such as one or more air cushions, a neoprene sleeve, or various other types of cushions, if desired. As shown in FIGS. 1, 3, and 8, some Velcro® dots 80 are adhered to the inner surface of this brace 10 in order to help secure such cushioning. Otherwise, the inner surface of the upper portion of the brace 10 preferably is smooth.

Figure 9:
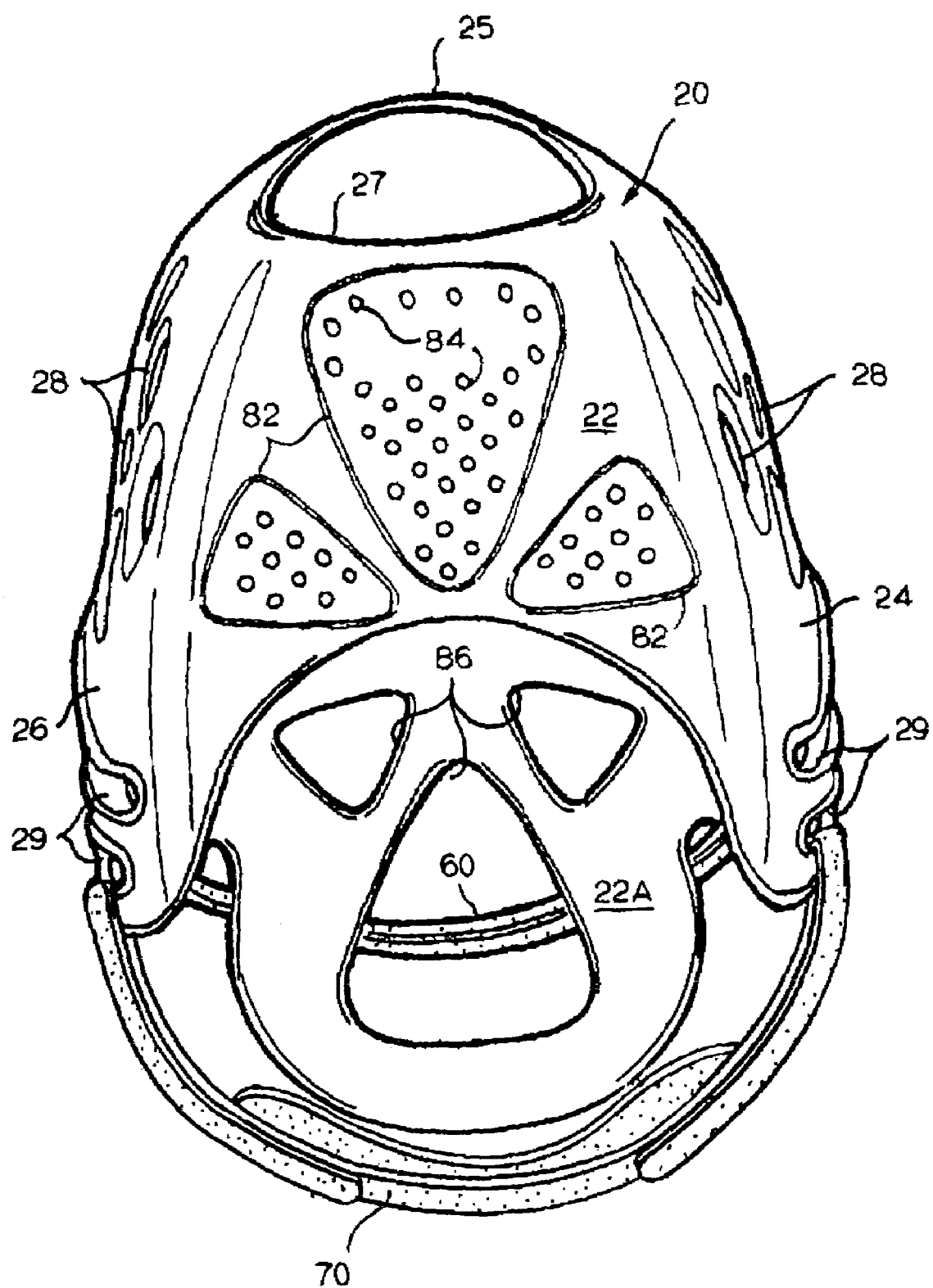
FIG. 9 is a bottom view of the brace of FIG. 1.

FIG. 9 is a view of the bottom of the ankle brace 10. The outside of the bottom portion 22 of the stirrup 20 has added texturing in order to provide some friction between the bottom portion 22 of the stirrup 20 and a shoe (or the ground, if a shoe is not being worn). The bottom portion 22 includes generally triangular shaped ridges 82 that protrude slightly downwardly from the bottom portion 22. Inside the ridges 82, there are circular recesses 84. The ridges 82 and recesses 84 provide an uneven bottom surface for increased friction. As shown in FIG. 8, on the inside of the bottom portion 20, there are slight indentations 85 corresponding to the ridges 82 protruding on the outside of the bottom portion 20. FIGS. 8 and 9 also show that the forward projection 22A on the bottom portion 22 defines triangular openings 86. The forward projection 22A is substantially thinner than the rest of the bottom 20. It should be noted that other texture arrangements, besides the ridges 82 and recesses 84 shown in FIG. 9, may be used on the outside of the bottom portion 22 to provide friction, or the outside of the bottom portion 22 could be smooth.

It will be obvious to those skilled in the foregoing description describes just one example of a product made in accordance with the present invention. It is understood that various modifications may be made without departing from the scope of the invention as claimed.

What is claimed is:

1. An ankle brace, comprising:
    a substantially U-shaped stirrup member, including a bottom portion adapted to extend under a wearer's foot and left and right upright portions adapted to extend upwardly along the left and right sides of the wearer's foot; and
    left and right pivot leg members pivotably attached to said left and right upright portions at left and right pivot points, respectively;
    wherein at least one of said members is made from a material having a flexural modulus greater than 10,000 psi and less than 80,000 psi.

2. An ankle brace as recited in claim 1, wherein said material has a tensile strength greater than 4,000 psi.

3. An ankle brace as recited in claim 2, wherein all of said members are made of material having a flexural modulus greater than 10,000 psi and less than 80,000 psi and a tensile strength greater than 4,000 psi.

4. An ankle brace as recited in claim 3, wherein the major portion of each of said left and right upright portions and said left and right pivot leg members is between 0.050 and 0.150 inches thick.

5. An ankle brace as recited in claim 3, and further comprising a rear cuff forming a unitary piece with said left and right pivot leg members.

6. An ankle brace as recited in claim 5, wherein said material is a polyurethane.

7. An ankle brace as recited in claim 1, wherein said material has a flexural modulus less than 50,000 psi.

8. An ankle brace, comprising:
    a substantially U-shaped stirrup, including a bottom portion adapted to extend under a wearer's foot and left and right upright portions adapted to extend upwardly along the left and right sides of the wearer's foot;
    left and right pivot legs pivotably attached to said left and right upright portions at left and right pivot points, respectively; and
    a cuff forming a unitary piece with said left and right pivot legs, wherein said cuff defines an upper band portion and a lower band portion, one of said upper and lower band portions being made of thinner material than the other of said upper and lower band portions.

9. An ankle brace as recited in claim 8, wherein said cuff defines indentations at its center top and bottom edges which reduce the height of said cuff at its center.

10. An ankle brace as recited in claim 8, wherein said cuff has upper and lower edges, and one of said upper and lower band portions that is made of thinner material forms one of said upper and lower edges of said cuff.

11. An ankle brace as recited in claim 10, wherein said one band portion that is made of thinner material is said lower band portion, and it forms the lower edge of said cuff.

12. An ankle brace as recited in claim 10, wherein said cuff defines indentations at its center top and bottom edges which reduce the height of said cuff at its center.

13. A method for securing an article of footwear on the wearer's foot, comprising the steps of:
    providing an article of footwear including a substantially U-shaped stirrup including a bottom portion adapted to extend under the wearer's foot and left and right upright portions adapted to extend along the left and right sides of the wearer's foot;
    providing left and right pivot legs pivotably attached to said left and right upright portions at left and right pivot points, respectively, each of said pivot legs having an outer surface and an inner surface and a front side, with a front opening being defined between the front sides of said left and right pivot legs, and a rear cuff extending between said left and right pivot legs;
    one of said pivot legs defining first and second vertical slots, with said first vertical slot being closer to the front side of its respective pivot leg than said second vertical slot, and the other of said pivot legs defining a third vertical slot; and
    taking a strap having first and second ends and placing the first end of the strap forward of said first vertical slot, with the strap extending from its first end into said first vertical slot and out said second vertical slot and wrapping over the first end of the strap, with the central portion of the strap extending across the front opening, and the second end of the strap extending through the third vertical slot, and securing the second end of said strap to the central portion of the strap by means of a hook and loop fastener.

14. A method for securing an article of footwear on the wearer's foot as recited in claim 13, including the step of securing the first end of said strap by friction.

15. A method for securing an article of footwear on the wearer's foot as recited in claim 14, wherein the second end of the strap is secured to the front surface of the central portion of the strap.

* * * * *